United States Patent
Atsumi et al.

[11] 3,962,446
[45] June 8, 1976

[54] ANALGESIC COMPOSITIONS CONTAINING 2-CYANOALKYLBENZOMORPHAN DERIVATIVES AND SALTS THEREOF

[75] Inventors: Toshio Atsumi, Saitama; Kenji Kobayashi; Yoshiaki Takebayashi, both of Takarazuka; Hisao Yamamoto, Nishinomiya, all of Japan

[73] Assignee: Sumitomo Chemical Company, Limited, Japan

[22] Filed: Nov. 13, 1974

[21] Appl. No.: 523,412

Related U.S. Application Data

[60] Continuation-in-part of Ser. No. 404,984, Oct. 10, 1973, abandoned, which is a division of Ser. No. 255,805, May 22, 1972, Pat. No. 3,793,332.

[30] Foreign Application Priority Data

May 21, 1971  Japan............... 46-34896
Dec. 20, 1971  Japan............... 46-103839

[52] U.S. Cl. ............................... 424/260
[51] Int. Cl.² ........................... A61K 31/485
[58] Field of Search ............ 424/267, 260

[56] References Cited
UNITED STATES PATENTS

| | | | |
|---|---|---|---|
| 3,372,165 | 3/1968 | Archer,.................. | 260/294.7 |
| 3,449,331 | 6/1969 | Clarke et al. .......... | 260/240 |
| 3,449,332 | 6/1969 | Clarke et al. .......... | 260/240 |
| 3,480,638 | 11/1969 | Block et al............. | 260/294.3 |
| 3,558,638 | 1/1971 | Clarke et al. ......... | 260/294.3 |
| 3,634,433 | 1/1972 | Moriyama et al....... | 260/293.54 |
| 3,639,407 | 2/1972 | Clarke et al. ......... | 260/293.54 |
| 3,639,410 | 2/1972 | Albertson et al. ...... | 260/293.54 |

*Primary Examiner*—Stanley J. Friedman
*Attorney, Agent, or Firm*—Craig & Antonelli

[57] ABSTRACT

An analgesic composition comprising an analgesically effective amount of at least one 6,7-benzomorphan derivative of the formula:

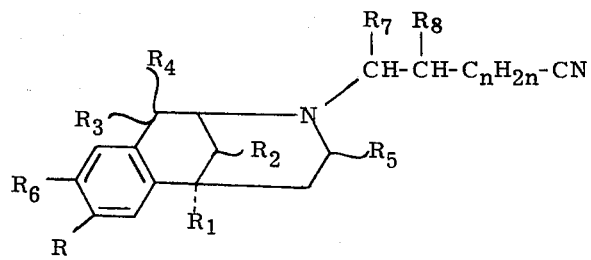

wherein R is a hydrogen atom, a hydroxyl group, a $C^1 - C^3$ alkoxy group or a $C^1 - C^8$ alkanoyloxy group; $R_1$ is a hydrogen atom, a $C^1 - C^5$ alkyl group, a phenyl group, a halophenyl group, an alkylphenyl group wherein the alkyl moiety has 1 to 3 carbon atoms, an alkoxyphenyl group wherein the alkoxy moiety has 1 to 3 carbon atoms, a trifluoromethylphenyl group, an alkylthiophenyl group wherein the alkylthio moiety has 1 to 3 carbon atoms or a group of the formula $(C_mH_{2m-p+1}) - (R_9)_p$ wherein $m$ is an integer of 1 – 6, $p$ is an integer of 1 – 2 and $R_9$ is a $C^1 - C^3$ alkoxy group; $R_2$ is a hydrogen atom or a $C^1 - C^3$ alkyl group; $R_3$ is a hydrogen atom, a $C^1 - C^3$ alkyl group, a phenyl group or an alkoxyphenyl group wherein the alkoxy moiety has 1 to 3 carbon atoms; $R_4$ is a hydrogen atom or a hydroxyl group, or $R_3$ and $R_4$ may form a $C^1 - C^3$ alkylidene group or a carbonyl group together with a carbon atom to which these substituents are bonded; $R_5$ is a hydrogen atom or $C^1 - C^3$ alkyl group; $R_6$ is a hydrogen atom or a methyl group; $R_7$ and $R_8$ are independently a hydrogen atom or a $C^1 - C^2$ alkyl group; and $n$ is an integer of 0 – 2; or an acid addition salt thereof, and a pharmaceutically acceptable carrier or diluent, is disclosed.

17 Claims, No Drawings

ANALGESIC COMPOSITIONS CONTAINING 2-CYANOALKYLBENZOMORPHAN DERIVATIVES AND SALTS THEREOF

This is a continuation-in-part application of Ser. No. 404,984, filed Oct. 10, 1973, now abandoned, which is a division of application of Ser. No. 255,805, filed May 22, 1972 and now Pat. No. 3,793,332.

The present invention relates to an analgesic composition comprising at least one of benzomorphan derivatives and their non-toxic pharmaceutically acceptable salts. More particularly, the invention relates to an analgesic composition comprising a pharmaceutically effective amount of at least one of benzomorphan derivatives of the following formula and their non-toxic pharmaceutically acceptable acid addition salts as an active ingredient, and a pharmaceutically acceptable carrier or diluent:

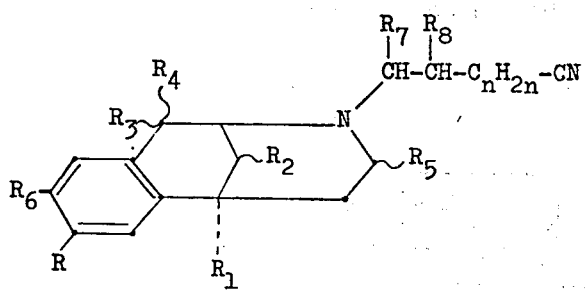

[I]

wherein R is a hydrogen atom, a hydroxyl group, a $C^1 - C^3$ alkoxy group or an acyloxy group such as $C^1 - C^8$ alkanoyloxy; $R_1$ is a hydrogen atom, a $C^1 - C^5$ alkyl group, a phenyl group, a halophenyl group, an alkylphenyl group (wherein the alkyl moiety has 1 to 3 carbon atoms), an alkoxyphenyl group (wherein the alkoxy moiety has 1 to 3 carbon atoms), a trifluoromethylphenyl group, an alkylthiophenyl group (wherein the alkylthio moiety has 1 to 3 carbon atoms) or a group of the formula: $(C_mH_{2m-p+1}) - (R_9)_p$ (wherein $m$ is an integer of 1 – 6, $p$ is an integer of 1 – 2 and $R_9$ is a $C^1 - C^3$ alkoxy group); $R_2$ is a hydrogen atom or a $C^1 - C^3$ alkyl group; $R_3$ is a hydrogen atom, a $C^1 - C^3$ alkyl group, a phenyl group or an alkoxyphenyl group (wherein the alkoxy moiety has 1 to 3 carbon atoms); $R_4$ is a hydrogen atom or a hydrogen group, or $R_3$ and $R_4$ may form a $C^1 - C^3$ alkylidene group or a carbonyl group together with a carbon atom to which these substituents are bonded; $R_5$ is a hydrogen atom or a $C^1 - C^3$ alkyl group; $R_6$ is a hydrogen atom or a methyl group; $R_7$ and $R_8$ are independently a hydrogen atom or a $C^1 - C^2$ alkyl group; and $n$ is an integer of 0 – 2.

Hitherto, many benzomorphan derivatives (e.g. phenazocine, pentazocine) have been developed as analgesic drugs but most of them have addiction and produce narcotic symptoms such as cessation of locomotor activity and stupor at their usual dosages.

It has been found that the benzomorphan derivatives of the formula [I] and acid addition salts thereof are useful as analgesic and pain-relieving agents without showing any drug dependency in animal tests.

Accordngly, a main object of the invention is to provide analgesic compositions comprising an analgesically effective amount of the 2-cyanoalkyl-6,7-benzomorphan derivative of the formula [I] or its non-toxic pharmaceutically acceptable acid addition salt as an active ingredient, and a pharmaceutically acceptable carrier or diluent.

The 2-cyanoalkyl-6,7-benzomorphan derivatives of the formula [I] and acid addition salts thereof can be administered orally, parenterally or rectally in total daily doses ranging from about 0.2 to 200 mg/man.

To this purpose, these compounds may be formulated, for example, to suitable pharmaceutical compositions such as granules, tablets, coated tablets, capsules, syrups, emulsions, suspensions, injections or suppositories.

The compositions for oral administration comprise carriers or excipients conventionally used in an ordinary pharmaceutical art. Thus, for example, suitable tabletting adjuvants include calcium carbonate, calcium phosphate, corn starch, potato starch, sucrose, lactose, talc, magnesium stearate and gum acacia.

For parenteral administration, the carrier may be sterile, parenterally acceptable liquid such as sterile water, essential oil such as peanut oil, corn oil or nonaqueous solvent such as polyethylene glycol, polypropylene glycol.

Compositions for rectal administration may take a form of suppositories and the carrier comprises a conventional suppository base such as polyethylene glycol lanolin or coconut butter.

Advantageously, the compositions may be formulated to dosage units, each unit being adapted to supply a fixed dose of the active ingredient. Tablets, coated tablets, capsules, ampoules and suppositories, mentioned above, are examples of suitable dosage unit forms. Each dosage unit for oral or rectal administration preferably contains 1 to 200 mg, and especially 5 to 100 mg, of the active ingredient and each dosage unit for parenteral administration contains 0.2 to 200 mg, preferably 0.5 to 50 mg, of the active ingredient according to the invention.

According to the invention, the 2-cyanoalkyl-6,7-benzomorphan derivative [I] can be prepared by reacting a 6,7-benzomorphan derivative of the formula:

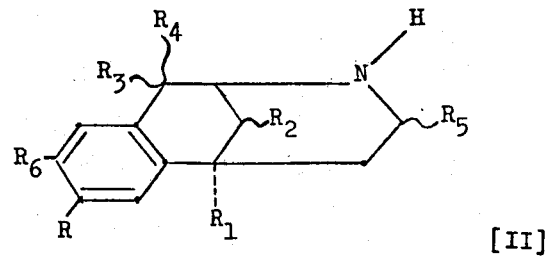

[II]

wherein R, $R_1$, $R_2$, $R_3$, $R_4$, $R_5$ and $R_6$ are each as defined above with a cyanide derivative of the formula:

$$A-C_nH_{2n}-CN \qquad [III]$$

wherein $n$ is as defined above and A is a group of the formula:

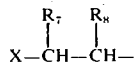

(wherein $R_7$ and $R_8$ are each as defined above and X is a halogen atom), or $n$ is 0 and A is a group of the formula:

(wherein $R_7$ and $R_8$ are each as defined above).

The starting 6,7-benzomorphan derivative [II] is known and can be prepared by demethylating the corresponding 2-methyl-6,7-benzomorphan derivative. Thus, for example, U.S. Pat. No. 3,138,603 discloses a process shown by the following formulae:

wherein R' is a methoxy group or an acetoxy group.

For the production of the 2-methyl-6,7-benzomorphan derivative represented by the formula:

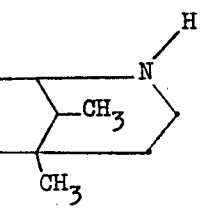

wherein R, $R_1$, $R_2$, $R_3$, $R_4$, $R_5$ and $R_6$ are each as defined above, there are known some processes, among which a typical process is shown in the following scheme:

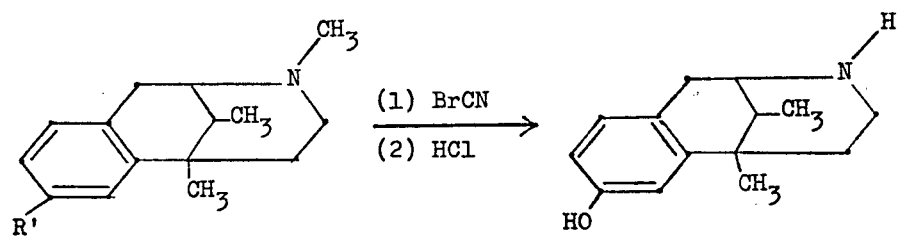

Scheme 1

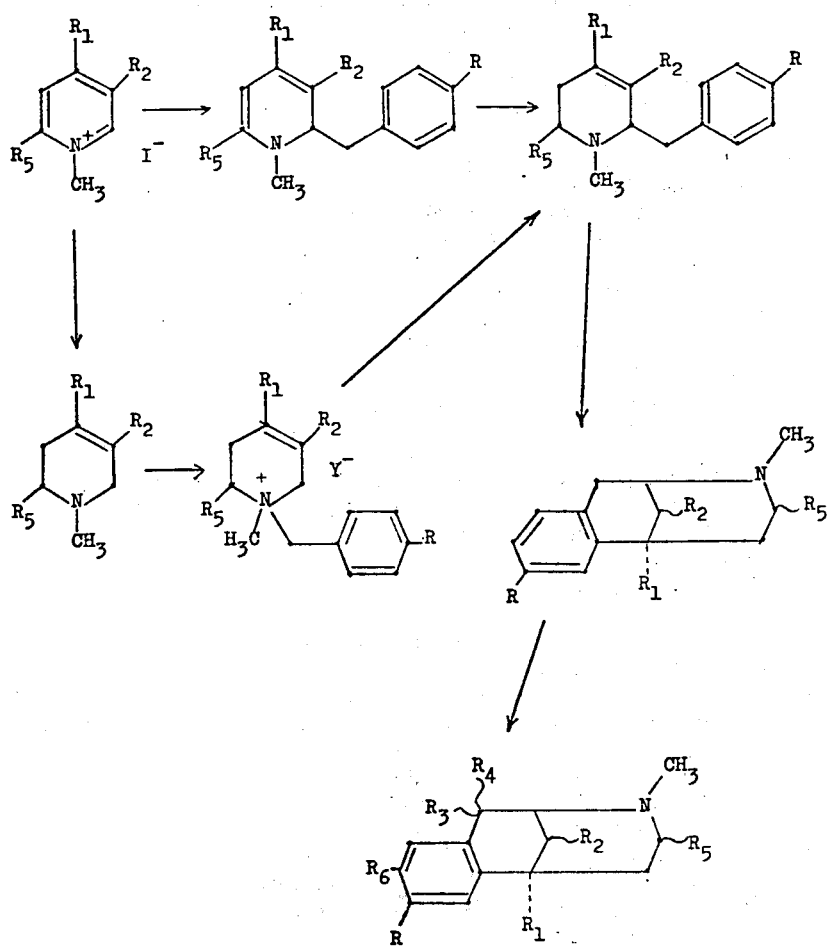

wherein R, $R_1$, $R_2$, $R_3$, $R_4$, $R_5$ and $R_6$ are each as defined above and Y is a halogen atom. Another typical process is shown in the following scheme:

Scheme 2

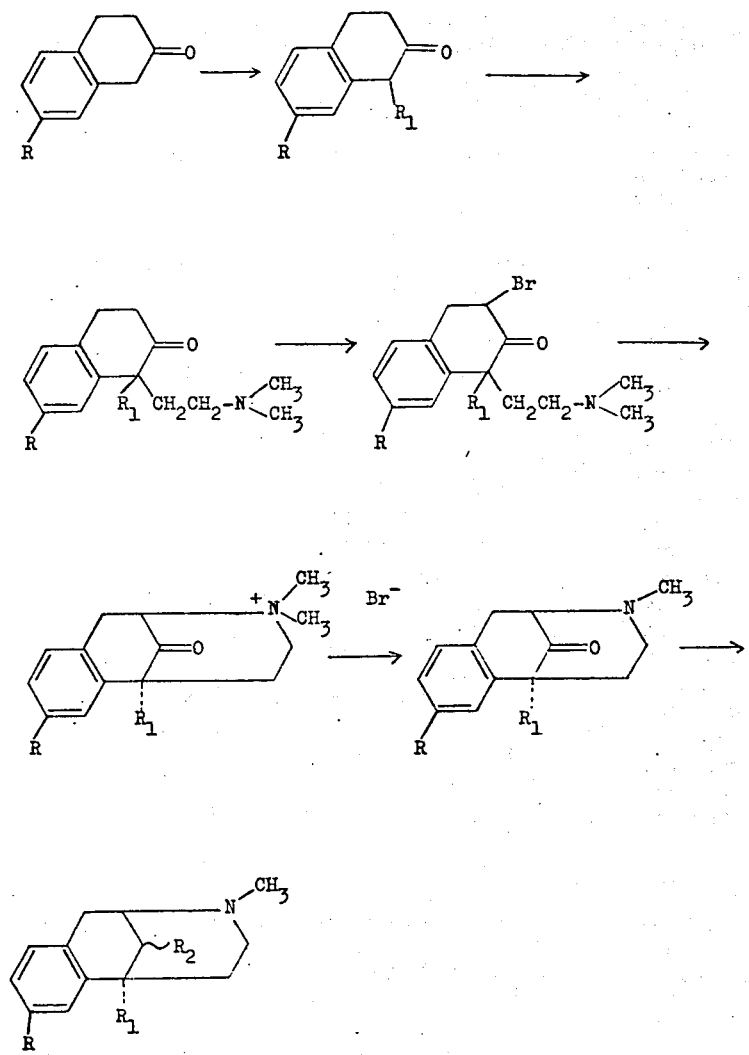

wherein R, $R_1$ and $R_2$ are each as defined above.

The reaction of the 6,7-benzomorphan derivative [II] with the cyanide derivative

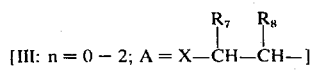

[III: n = 0 – 2; A = X—CH—CH—]

is usually carried out in an inert solvent (e.g. n-hexane, benzene, toluene, xylene, chloroform, dimethylformamide, methanol, ethanol, isopropanol). The presence of a basic substance (e.g. sodium carbonate, potassium carbonate, sodium bicarbonate, potassium bicarbonate, sodium hydroxide, potassium hydroxide, sodium amide, sodium hydride, pyridine, triethylamine) in the reaction is preferred. The reaction proceeds at a temperature of 20° to 200°C, preferably 50° to 150°C. The reaction product is readily recovered from the reaction mixture by a conventional separation procedure such as filtration and precipitation.

The reaction of the 6,7-benzomorphan derivative [II] with the cyanide derivative

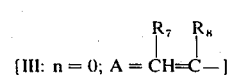

[III: n = 0; A = CH=C—]

is per se novel and may be called as the modified Michael Addition. By this reaction, the 2-cyanoalkyl-6,7-benzomorphan derivative [I] can be produced in an excellent yield and a high purity by a simple operation. The reaction is carried out in the absence or presence of an appropriate solvent (e.g. methanol, ethanol, ether, chloroform, methylene chloride, benzene, toluene, xylene, dimethylformamide). Further, there may be used a catalyst, of which examples are Triton B, sodium methoxide, sodium amide, potassium hydroxide, etc. The reaction proceeds at a temperature from about room temperature to the boiling point of the solvent employed.

For the production of the 2-cyanoalkyl-6,7-benzomorphan derivative [I: R = acyloxy], the corresponding 2-cyanoalkyl-6,7-benzomorphan derivative [I: R = hydroxy] may be acylated by a per se conventional procedure, e.g. treating with an acid anhydride or acyl halide.

When $R_2$ is alkyl, the 2-cyanoalkyl-6,7-benzomorphan derivative [I] has two stereo isomers, i.e. cis isomer ($R_2$ being α-configuration) and trans isomer ($R_2$ being β-configuration). Each of these isomers can be separated and purified by a per se conventional procedure such as fractional crystallization, fractional distillation or column chromatography. Alternatively, each of these isomers may be produced from the corresponding cis or trans isomer of the 6,7-benzomorphan derivative [II] by reacting the same with the cyanide derivative [III]. Still, each of the said isomers has asymmetric carbon atoms, and there can be obtained four optically active isomers (i.e. (+)-cis, (−)-cis, (+)-trans, (−)-trans) by a conventional optical resolution procedure.

The 2-cyanoalkyl-6,7-benzomorphan derivative [I] possesses a basic nitrogen atom in the fundamental structure and hence various acid addition salts thereof can be formed. The acid addition salts can be obtained by the use of organic and inorganic acids such as formic acid, acetic acid, propionic acid, butyric acid, malic acid, fumaric acid, succinic acid, glutamic acid, tartaric acid, oxalic acid, citric acid, lactic acid, maleic acid, hydroxymaleic acid, glycolic acid, gluconic acid, glucuronic acid, saccharic acid, ascorbic acid, phenylacetic acid, benzoic acid, p-aminobenzoic acid, phthalic acid, salicyclic acid, anthranilic acid, p-hydroxybenzoic acid, p-aminosalicyclic acid, picolinic acid, 3-hydroxy-2-naphthoic acid, 3-indolacetic acid, barbituric acid, sulfamic acid, quininic acid, tropic acid, methanesulfonic acid, ethanesulfonic acid, benzenesulfonic acid, p-toluenesulfonic acid, hydroxyethanesulfonic acid, hydrofluoric acid, hydrochloric acid, hydrobromic acid, hydroiodic acid, perchloric acid, nitric acid, sulfuric acid, phosphoric acid, 1-(4-chlorobenzoyl)-2-methyl-5-methoxy-3-indolylacetic acid, 1-cinnamoyl-2-methyl-5-methoxy-3-indolylacetic acid, 1-(3,4-methylenedioxybenzoyl)-2-methyl-5-methoxy-3-indolyacetic acid, 1-cinnamoyl-2-methyl-5,6-methylenedioxy-3-indolylacetic acid, 1-(4-chlorobenzoyl)-2-methyl-5,6-methylenedioxy-3-indolylacetic acid, 1-(4-fluorobenzoyl)-2-methyl-5,6-methylenedioxy-3-indolylacetic acid and the like.

According to the present invention, the following 2-cyanoalkyl-6,7-benzomorphan derivatives [I], and acid addition salts thereof, can be obtained:

2-(β-Cyanoethyl)-6,7-benzomorphan
2-(β-Cyanoethyl)-5,9-dimethyl-6,7-benzomorphan
2-(β-Cyanoethyl)-5-methyl-6,7-benzomorphan
2′-Hydroxy-2-(β-cyanoethyl)-6,7-benzomorphan
2′-Hydroxy-2-(β-cyanoethyl)-5-methyl-6,7-benzomorphan
2′-Hydroxy-2-(β-cyanoethyl)-5,8,9-trimethyl-6,7-benzomorphan
2′-Hydroxy-2-(β-cyanoethyl)-3,5-dimethyl-6,7-benzomorphan
2′-Hydroxy-2-(β-cyanoethyl)-5-phenyl-6,7-benzomorphan
2′-Hydroxy-2-(β-cyanoethyl)-5,9-dimethyl-8-oxo-6,7-benzomorphan
2′-Hydroxy-3′-methyl-2-(β-cyanoethyl)-5,9-dimethyl-6,7-benzomorphan
2′-Hydroxy-2-(β-cyanoethyl)-5,9-dimethyl-6,7-benzomorphan
2′-Hydroxy-3′-methyl-2-(β-cyanoethyl)-5,9-diethyl-6,7-benzomorphan
2′-Methoxy-2-(β-cyanoethyl)-5,9-dimethyl-6,7-benzomorphan
2′-Acetoxy-2-(β-cyanoethyl)-5,9-dimethyl-6,7-benzomorphan
2′-Hydroxy-2-(β-cyanoethyl)-5-(β-methoxyethyl)-6,7-benzomorphan
2′-Hydroxy-2-(β-cyanoethyl)-5,9-diethyl-6,7-benzomorphan
2′-Hydroxy-2-(β-cyanoethyl)-5-methyl-9-ethyl-6,7-benzomorphan
2′-Hydroxy-2-(β-cyanoethyl)-5-ethyl-9-methyl-6,7-benzomorphan
2′-Hydroxy-2-(α-methyl-β-cyanoethyl)-5-methyl-6,7-benzomorphan
2′-Hydroxy-2-(α-methyl-β-cyanoethyl)-5,9-dimethyl-6,7-benzomorphan
2′-Hydroxy-2-(β-methyl-β-cyanoethyl)-5-methyl-6,7-benzomorphan
2′-Hydroxy-2-(β-methyl-β-cyanoethyl)-5,9-dimethyl-6,7-benzomorphan
2′-Hydroxy-2-(α-ethyl-β-cyanoethyl)-5,9-dimethyl-6,7-benzomorphan
2′-Methoxy-2-(α-methyl-β-cyanoethyl)-5,9-dimethyl-6,7-benzomorphan
2′-Hydroxy-2-(β-cyanoethyl)-9methyl-6,7-benzomorphan
2′-Hydroxy-2-(γ-cyanopropyl)-5,9-dimethyl-6,7-benzomorphan
2′-Methoxy-2-(γ-cyanopropyl)-5,9-dimethyl-6,7-benzomorphan
2′-Methoxy-2-(β-methyl-β-cyanopropyl)-5,9-dimethyl-6,7-benzomorphan
2′-Acetoxy-2-(γ-cyanopropyl)-5,9-dimethyl-6,7-benzomorphan
2′-Acetoxy-2-(β-methyl-γ-cyanopropyl)-5,9-dimethyl-6,7-benzomorphan
2-(γ-Cyanopropyl)-5,9-dimethyl-6,7-benzomorphan
2-(β-Methyl-γ-cyanopropyl)-5,9dimethyl-6,7-benzomorphan
2′-Hydroxy-2-(γ-cyanopropyl-5-methyl-6,7-benzomorphan
2′-Hydroxy-2-(γ-cyanopropyl)-9-methyl-6,7-benzomorphan
2′-Hydroxy-2-(γ-cyanopropyl)-6,7-benzomorphan
2-(γ-Cyanopropyl)-5-methyl-6,7-benzomorphan
2-(γ-Cyanopropyl)-6,7-benzomorphan
2′-Hydroxy-2-(γ-cyanopropyl)-5,8,9-trimethyl-6,7-benzomorphan
2′-Hydroxy-3′-methyl-2-(γ-cyanopropyl)-5,9-dimethyl-6,7-benzomorphan
2′-Hydroxy-2-(γ-cyanopropyl)-5,9-dimethyl-8-oxo-6,7-benzomorphan
2′-Hydroxy-2-(γ-cyanopropyl)-3,5-dimethyl-6,7-benzomorphan
2′-Hydroxy-2-(γ-cyanopropyl)-5-phenyl-6,7-benzomorphan
2′-Hydroxy-2-(γ-cyanopropyl)-5-(β-methoxyethyl)-6,7-benzomorphan
2′-Hydroxy-2-(δ-cyanobutyl)-5,9-dimethyl-6,7-benzomorphan
2′-Hydroxy-2-(δ-cyanobutyl)-6,7-benzomorphan 2'-Hydroxy-2-(δ-cyanobutyl)-5-methyl-6,7-benzomorphan 2'-Hydroxy-2-(δ-cyanobutyl)-5,9-dimethyl-8-methylene-6,7-benzomorphan 2'-Hydroxy-3'-methyl-2-(δ-cyanobutyl)-5,9-dimethyl-6,7-benzomorphan 2-(δ-Cyanobutyl)-6,7-benzomorphan 2'-Hydroxy-2-(γ-cyanopropyl-5,9-diethyl-6,7-benzomorphan 2'-Hydroxy-2-(γ-cyanopropyl)-5-methyl-9-ethyl-6,7-benzomorphan 2'-Hydroxy-2-(γ-cyanopropyl)-5-ethyl-9-methyl-6,7benzomorphan 2'-Hydroxy-2-(γ-cyanopropyl)-5-ethyl-6,7-benzomorphan 2'-Hydroxy-2-(β-methyl-γ-cyanopropyl)-5,9-dimethyl-6,7-benzomorphan 2'-Hydroxy-2-(β-methyl-γ-cyanopropyl)-5-ethyl-9-methyl-6,7-benzomorphan 2'-Methoxy-2-(γ-cyanopropyl)-5,9-diethyl-6,7-benzomorphan 2'-Propionyloxy-2-(γ-cyanopropyl)-5-ethyl-9-methyl-6,7-benzomorphan, etc.

6,7-Benzomorphan derivatives such as 2'-hydroxy-2,5,9-trimethyl-6,7-benzomorphan (U.S. Pat. No. 3,138,603) have a potent analgesic activity but show an addiction liability. On account of this addiction liability, these analgesics are severely restricted in a therapeutic use. Surprisingly, the 2-cyanoalkyl-6,7-benzomorphan derivatives [I] (e.g. 2'-hydroxy-2-(β-cyanoethyl)-5,9-dimethyl-6,7-benzomorphan, 2'-hydroxy-2-(β-cyanoethyl)-5-methyl-6,7-benzomorphan, 2'-acetoxy-2-(β-cyanoethyl)-5,9-dimethyl-6,7-benzomorphan, 2'-hydroxy-2-(γ-cyanopropyl)-5-ethyl-9-methyl-6,7-benzomorphan) do not show addiction in long term animal tests. When, for example, these compounds were administrated orally or subcutaneously to rats everday for over one month, the animals did not produce any physical dependency as shown in Table I.

Table I

| Compound | Dose (mg/kg/day for 4 weeks) | Abstinence syndrome |
|---|---|---|
| 2'-Hydroxy-2-(β-cyanoethyl)-5,9-dimethyl-6,7-benzomorphan | 20 | – |
| 2'-Hydroxy-2-(β-cyanoethyl)-5-methyl-6,7-benzomorphan | 20 | – |
| 2-(β-Cyanoethyl)-5-methyl-6,7-benzomorphan | 20 | – |
| 2'-Acetoxy-2-(β-cyanoethyl)-5,9-dimethyl-6,7-benzomorphan | 20 | – |
| 2'-Hydroxy-2-(γ-cyanopropyl)-5,9-dimethyl-6,7-benzomorphan | 20 | – |
| 2'-Hydroxy-2-(γ-cyanopropyl)-5,9-diethyl-6,7-benzomorphan | 20 | – |
| 2'-Hydroxy-2-(γ-cyanopropyl)-5-methyl-9-ethyl-6,7-benzomorphan | 20 | – |
| 2'-Hydroxy-2-(γ-cyanopropyl)-5-ethyl-9-methyl-6,7-benzomorphan | 20 | – |
| Morphine | 20 | +++ |
| 2'-Hydroxy-2,5,9-trimethyl-6,7-benzomorphan | 20 | ++ |

Note: Groups of male rats of Wistar strain (bodyweight, 150 g), each group consisting of 20 male rats, were subcutaneously given the test compound twice a day for 4 consecutive weeks. On the next day after drug withdrawal, the bodyweight was measured. The symbols have the following meanings: +++, severe decrease (about 5% decrease); ++, moderate decrease; +, mild decrease; –, no decrease. The marked decrease is taken as an indication of the possession of a narcotic property by the test compound.

Further, the 2-cyanoalkyl-6,7-benzomorphan derivatives [I] show a strong analgesic activity. In a subcutaneous writhing test, for instance, they exhibited much more potent analgesic action than pentazocin (i.e. 2'-hydroxy-2-(3'''-methyl-2''butenyl)-5,9-dimethyl-6,7-benzomorphan), which is one of the strongest, commercial analgesics, as shown in Table II.

Table II

| Compound | $ED_{50}$ (mg/kg) |
|---|---|
| 2'-Hydroxy-2-(β-cyanoethyl)-5,9-dimethyl-6,7-benzomorphan | 0.9 |
| 2'-Hydroxy-2-(β-cyanoethyl)-5-methyl-6,7-benzomorphan | 2.9 |
| 2'-Hydroxy-2-(γ-cyanopropyl)-5,9-dimethyl-6,7-benzomorphan | 3.0 |
| 2'-Hydroxy-2-(γ-cyanopropyl)-5-methyl-9-ethyl-6,7-benzomorphan | 1.5 |
| 2'-Hydroxy-2-(γ-cyanopropyl)-5,9-diethyl-6,7-benzomorphan | 0.3 |
| 2'-Hydroxy-2-(γ-cyanopropyl)-5-ethyl-9-methyl-6,7-benzomorphan | 0.19 |
| 2'-Acetoxy-2-(β-cyanoethyl)-5,9-dimethyl-6,7-benzomorphan | 0.5 |
| Morphine | 1.4 |
| Methylmorphine | 14.0 |
| 2'-Hydroxy-2,5,9-trimethyl-6,7-benzomorphan | 3.5 |
| Pentazocine (2'-hydroxy-2-(3''-methyl-2''-butenyl)-5,9-dimethyl-6,7-benzomorphan) | 17.5 |

Note: The test was based on the specific antagonism of the test compound to the typical syndrome produced by intraperitoneal injection of 0.6% aqueous acetic acid. The syndrome was characterized by intermittent contractions of the abdomen, twisting and turning of the trunk and extension of the hind legs. A group of 5 mice was used for each dose level. The test compound was administered subcutaneously 20 minutes before the injection of acetic acid. The number of mice which showed no pain response was recorded. The $ED_{50}$ value was calculated according to the Litchfeld-Wilcoxon's method.

Practical and presently preferred embodiments of the present invention are shown in the following Examples. Modifications of the procedures shown in these Examples will be obvious to those skilled in the art, and these Examples do not limit the scope of the invention.

EXAMPLE 1

2'-Hydroxy-2-(β-cyanoethyl)-5,9-dimethyl-6,7-benzomorphan

A mixture of 1.1 g of 2'-hydroxy-5,9-dimethyl-6,7-benzomorphan, 0.5 g of sodium bicarbonate, 0.42 g of β-chloropropionitrile and 20 ml of dimethylformamide is stirred at 120° – 160°C for 4 hours. The precipitate produced is filtered off. The filtrate is concentrated under reduced pressure to remove the dimethylformamide, and water is added thereto. The precipitate obtained is recrystallized from methanol to yield 2'-hydroxy-2-(β-cyanoethyl)-5,9-dimethyl-6,7-benzomorphan, m.p. 165.5°C.

$IR\nu_{paraffin}^{cm^{-1}}$: 2640, 2240, 1610, 1580, 1495, 1240.

Anal. Calcd. for $C_{17}H_{22}N_2O$: C, 75.52; H, 8.20; N, 10.36 %. Found: C, 75.40; H, 8.13; N, 10.31 %.

EXAMPLE 2

2'-Hydroxy-2-(γ-cyanopropyl)-5,9-dimethyl-6,7-benzomorphan

To a mixture of 1.1 g of 2'-hydroxy-5,9-dimethyl-6,7-benzomorphan, 0.5 g of sodium bicarbonate and 20 ml of dimethylformamide is added 0.52 g of γ-chlorobutyronitrile. The resultant mixture is stirred at 120° – 160°C for 4.5 hours. The solvent is removed under reduced pressure to leave a residue, to which water is added. The mixture is extracted with ether, and the extract is washed, dried over anhydrous sodium sulfate and filtered. The filtrate is concentrated to dryness to give 2'-hydroxy-2-(γ-cyanopropyl)-5,9-dimethyl-6,7-benzomorphan as a viscous liquid.

$IR\nu_{liq.}^{cm^{-1}}$: 2250, 1670 (weak), 1613, 1585, 1500.

T.L.C. (silica gel) Rf value: 0.55 (acetone).

EXAMPLE 3

2'-Acetoxy-2-(γ-cyanopropyl)-5,9-dimethyl-6,7-benzomorphan

A mixture of 1.2 g of 2'-hydroxy-2-(γ-cyanopropyl)-5,9-dimethyl-6,7-benzomorphan hydrochloride, 0.31 g of anhydrous sodium acetate and 10 ml of acetic anhydride is stirred at 100° – 120°C for an hour, cooled and poured into ice water. The resultant mixture is made alkaline with aqueous potassium hydroxide (50 %) while keeping ice cold, and the liberated base is shaken quickly into ether. The ether extract is washed, dried and filtered. The filtrate is evaporated to dryness to yield 1.25 g of 2'-acetoxy-2-(γ-cyanopropyl)-5,9-dimethyl-6,7-benzomorphan as a yellow liquid.

$IR\nu_{liq.}^{cm^{-1}}$: 2240, 1760, 1637, 1605, 1580, 1495, 1210.

EXAMPLE 4

2'-Hydroxy-2-(γ-cyanopropyl)-5-methyl-9-ethyl-6,7-benzomorphan

To a mixture of 0.58 g of 2'-hydroxy-5-methyl-9-ethyl-6,7-benzomorphan, 0.32 g of sodium bicarbonate and 15 ml of dimethylformamide is added 0.28 g of γ-chlorobutyronitrile. The resultant mixture is refluxed for 4 hours. The precipitate produced is filtered off. The filtrate is concentrated under reduced pressure to remove the solvent, and water is added thereto. The precipitate obtained is recrystallized from ethyl acetate to give 2'-hydroxy-2-(γ-cyanopropyl)-5-methyl-9-ethyl-6,7-benzomorphan, m.p. 154° – 157°C.

$IR\nu_{paraffin}^{cm^{-1}}$: 2640, 2230, 1611, 1573, 1496, 923, 790.

Anal. Calcd. for $C_{19}H_{26}N_2O$: C, 76.47; H, 8.78; N, 9.39 %. Found: C, 76.73; H, 8.96; N, 9.19 %.

EXAMPLE 5

2'-Hydroxy-2-(δ-cyanobutyl)-5,9-dimethyl-6,7-benzomorphan

A mixture of 1.0 g of 2'-hydroxy-5,9-dimethyl-6,7-benzomorphan, 0.58 g of sodium bicarbonate, 0.59 g of δ-chlorovaleronitrile and 15 ml of dimethylformamide is refluxed for 4 hours. The precipitate produced is filtered off. The filtrate is concentrated under reduced pressure to leave a residue, to which water is added. The crude product is recrystallized from ethyl acetate to yield 2'-hydroxy-2-(δ-cyanobutyl)-5,9-dimethyl-6,7-benzomorphan, m.p. 158° – 161°C.

$IR\nu_{paraffin}^{cm^{-1}}$: 2600, 2225, 1610, 1575, 1495, 1270, 860, 802, 775.

Anal. Calcd. for $C_{19}H_{26}N_2O$: C, 76.47; H, 8.78; N, 9.39 %. Found: C, 76.31; H, 8.79; N, 9.21 %.

EXAMPLE 6

2-(β-Cyanoethyl)-5-methyl-6,7-benzomorphan

A solution of 1.0 g of 5-methyl-6,7-benzomorphan in 20 ml of absolute ether is added dropwise to 20 ml of acrylonitrile at room temperature. The resultant mixture is refluxed for 20 minutes and concentrated to dryness to give 2-(β-cyanoethyl)-5-methyl-6,7-benzomorphan as a brown oil. This free base is converted to the hydrochloride by treating with methanol-hydrochloric acid. The hydrochloride is recrystallized from acetone-methanol to give 2-(β-cyanoethyl)-5-methyl-6,7-benzomorphan hydrochloride, m.p. 213.5° – 215.0°C.

$IR\nu_{paraffin}^{cm^{-1}}$: 2420, 2240.

Anal. Calcd. for $C_{16}H_{21}N_2Cl$: C, 69.42; H, 7.64; N, 10.12; Cl, 12.81 %. Found: C, 69.72; H, 7.73; N, 10.10; Cl, 12.61 %.

EXAMPLE 7

2-(β-Cyanoethyl)-5,9-dimethyl-6,7-benzomorphan

A mixture of 2.01 g of 5,9-dimethyl-6,7-benzomorphan, 40 ml of absolute ether and 0.55 g of acrylonitrile is refluxed for one hour and concentrated to a yellow residue, which is distilled under reduced pressure to yield 1.6 g of 2-(β-cyanoethyl)-5,9-dimethyl-6,7-benzomorphan, b.p. 150° – 155°C/0.28 mmHg.

$IR\nu_{liq.}^{cm^{-1}}$: 2230, 1490.

A solution of 2-(β-cyanoethyl)-5,9-dimethyl-6,7-benzomorphan in ether is acidified with gaseous hydrogen chloride. The precipitate produced is collected by filtration and washed with ether. Recrystallization from acetone-methanol gives 2-(β-cyanoethyl)-5,9-dimethyl-6,7-benzomorphan hydrochloride, m.p. 238° – 240°C (decomposition).

$IR\nu_{paraffin}^{cm^{-1}}$: 2550, 2240, 965, 763, 750, 722

Anal. Calcd. for $C_{17}H_{23}N_2Cl$: C, 70.20; H, 7.97; N, 9.63; Cl, 12.19 %. Found: C, 70.32; H, 7.95; N, 9.84; Cl, 12.34 %.

EXAMPLE 8

2'-Hydroxy-2-(β-cyanoethyl)-5-methyl-6,7-benzomorphan

To a solution of 1.02 g of 2'-hydroxy-5-methyl-6,7-benzomorphan in 20 ml of methanol is added 10 ml of acrylonitrile. The resultant mixture is stirred at room temperature for 2 hours and concentrated to dryness to give crude 2'-hydroxy-2-(β-cyanoethyl)-5-methyl-6,7-benzomorphan. Recrystallization from ethyl acetate yields 2'-hydroxy-2-(β-cyanoethyl)-5-methyl-6,7-benzomorphan as prisms, m.p. 161° – 163°C.

$IR\nu_{paraffin}^{cm^{-1}}$: 2600, 2240, 1610, 1580, 1500.

Anal. Calcd. for $C_{16}H_{20}N_2O$: C, 74.96; H, 7.86; N, 10.93 %. Found: C, 74.66; H, 7.95; N, 10.98 %.

EXAMPLE 9

2'-Acetoxy-2-(β-cyanoethyl)-5,9-dimethyl-6,7-benzomorphan

A mixture of 1.0 g of 2'-hydroxy-2-(β-cyanoethyl)-5,9-dimethyl-6,7-benzomorphan and 10 ml of acetic anhydride is stirred at 100° – 110°C for one hour, cooled and poured into ice water. The mixture is made alkaline with aqueous potassium hydroxide (50%) while keeping ice cold and extracted quickly with ether. The ether extract is washed with saturated aqueous sodium chloride solution, dried over anhydrous sodium sulfate and filtered. The filtrate is concentrated to dryness to give 2'-acetoxy-2-(β-cyanoethyl)-5,9-dimethyl-6,7-benzomorphan as a yellow liquid.

$IR\nu_{liq.}^{cm^{-1}}$: 2250, 1755, 1620, 1580, 1492, 1375, 1010, 942.

EXAMPLES 10 to 12

The following compounds are obtained in accordance with the manner similar to that of Example 1:

2'-Hydroxy-2-(γ-cyanopropyl)-5-methyl-6,7-benzomorphan, m.p. 138° – 140°C;

2'-Hydroxy-3'-methyl-2-(β-cyanoethyl)-5,9-dimethyl-6,7-benzomorphan, m.p. 115° – 120°C;

2'-Hydroxy-2-(β-cyanoethyl)-5-phenyl-6,7-benzomorphan, m.p. 108° – 112°C.

EXAMPLES 13 to 15

The following compounds are obtained in accordance with the manner similar to that of Example 8:

2'-Hydroxy-2-(β-cyanoethyl)-5-methyl-9-ethyl-6,7-benzomorphan, m.p. 124° – 130°C;

2'-Hydroxy-2-(β-cyanoethyl)-5-ethyl-9-methyl-6,7-benzomorphan, m.p. 153° – 155°C;

2'-Hydroxy-2-(β-cyanoethyl)-5,9-diethyl-6,7-benzomorphan, m.p. 131° – 135°C.

EXAMPLE 16 to 31

In the same manner as above, the following compounds are obtained:

2'-Hydroxy-2-(γ-cyanopropyl)-5-phenyl-6,7-benzomorphan, m.p. 205° – 208°C;

2'-Hydroxy-2-(γ-cyanopropyl)-5-ethyl-6,7-benzomorphan, m.p. 176.5° – 179°C;

2'-Hydroxy-2-(γ-cyanopropyl)-5,9-diethyl-6,7-benzomorphan, m.p. 155° – 158°C;

2'-Hydroxy-2-(γ-cyanopropyl)-5-ethyl-9-methyl-6,7-benzomorphan, m.p. 172° – 175°C;

2'-Hydroxy-2-(γ-cyanopropyl)-6,7-benzomorphan, viscous liquid, $IR\nu_{liq.}^{cm^{-1}}$: 2240;

2'-Methoxy-2-(γ-cyanopropyl)-5,9-diethyl-6,7-benzomorphan hydrochloride, m.p. 224° – 226°C (decomposition);

2'-Hydroxy-2-(β-methyl-β-cyanoethyl)-5,9-dimethyl-6,7-benzomorphan, viscous liquid, $IR\nu_{liq.}^{cm^{-1}}$: 2242;

2'-Hydroxy-2-(β-cyanoethyl)-6,7-benzomorphan, viscous liquid, $IR\nu_{liq.}^{cm^{-1}}$: 2235;

2-(γ-Cyanopropyl)-6,7-benzomorphan hydrochloride, m.p. >240°C (decomposition);

2'-Hydroxy-2-(β-methyl-γ-cyanopropyl)-5,9-dimethyl-6,7-benzomorphan, viscous liquid, $n_D^{23}$: 1.5390, $IR\nu_{liq.}^{cm^{-1}}$: 2225;

2'-Hydroxy-2-(β-methyl-γ-cyanopropyl)-5-ethyl-9-methyl-6,7-benzomorphan, viscous liquid, $n_D^{24.5}$: 1.5281, $IR\nu_{liq.}^{cm^{-1}}$: 2240;

2'-Propionyloxy-2-(γ-cyanopropyl)-5-ethyl-9-methyl-6,7-benzomorphan oxalate, m.p. 180° – 181°C (decomposition);

2'-Hydroxy-2-(γ-cyanopropyl)-5-ethyl-9-methyl-6,7-benzomorphan 1-(4-chlorobenzoyl)-2-methyl-5-methoxy-3-indolylacetate, m.p. 89°C (decomposition);

2'-Hydroxy-2-(γ-cyanopropyl)-5-ethyl-9-methyl-6,7-benzomorphan 1-cinnamoyl-2-methyl-5-methoxy-3-indolylacetate, m.p. 93° – 103°C (decomposition);

2'-Hydroxy-2-(γ-cyanopropyl)-5-ethyl-9-methyl-6,7-benzomorphan 1-(3,4-methylenedioxybenzoyl)-2-methyl-5-methoxy-3-indolylacetate, m.p. 76° – 83°C (decomposition);

2'-Hydroxy-2-(γ-cyanopropyl)-5-ethyl-9-methyl6,7-benzomorphan 1-cinnamoyl-2-methyl-5,6-methylenedioxy-3-indolylacetate, m.p. 91° – 98°C (decomposition).

EXAMPLE 32

Ampoules (1):-

| | Each ampoule |
|---|---|
| 2'-Hydroxy-2-(γcyanopropyl) 5-ethyl-9-methyl-6,7-benzomorphan | 10 mg |
| Lactic acid | 12.5 mg |
| NaOH | 8.7 mg |
| Distilled water | ad. 1 ml |

Ampoules (2):-

| | Each ampoule |
|---|---|
| 2'-Hydroxy-2-(β-cyanoethyl)-5,9-dimethyl-6,7-benzomorphan | 10 mg |
| Glutamic acid | 5.4 mg |
| NaCl | 5.8 mg |
| conc.HCl | 1.4 mg |
| Distilled water | ad. 1 ml |

Ampoules (3):-

| | Each ampoule |
|---|---|
| 2'-Hydroxy-2-(γ-cyanopropyl)-5,9-dimethyl-6,7-benzomorphan | 10 mg |
| Lactic acid | 6.9 mg |
| NaOH | 9.5 mg |
| Distilled water | ad. 1 ml |

The active ingredient is dissolved in an adequate amount of the organic acid solution as prepared in advance, and then water is added thereto to make nearly a full volume. The pH is adjusted with an adequate amount of HCl or NaOH and then the total volume is adjusted with water. The solution is filled into ampoules and sterilized.

EXAMPLE 33

Tablets:-

| | Each tablet |
|---|---|
| 2'-Hydroxy-2-(γ-cyanopropyl)-5-ethyl-9-methyl-6,7-benzomorphan | 20 mg |
| Lactose | 120 mg |
| Corn starch | 30 mg |
| Magnesium stearate | 2.5 mg |
| Polyvinyl acetate | 2 mg |

The active ingredient is admixed with an adequate amount of lactose and wetted with a suitable amount of polyvinyl acetate-ethanol solution. The resultant wet substance is formulated into granules. The granules are dried, admixed with a small amount of calcium phosphate and talc and compressed to tablets.

EXAMPLE 34

Suppositories:-

| | Each suppository |
|---|---|
| 2'-Hydroxy-2-(γ-cyanopropyl)-5-ethyl-9-methyl-6,7-benzomorphan | 50 mg |
| Polyethylene glycol 6000 | 1900 mg |
| Polyethylene glycol 400 | 50 mg |

The active ingredient is dissolved in a suitable amount of polyethylene glycol suppository base with gentle heating, and the solution is casted to suppositories in an adequate mould.

What is claimed is:

1. An analgesic composition comprising an analgesically effective amount of at least one 6,7-benzomorphan derivative of the formula:

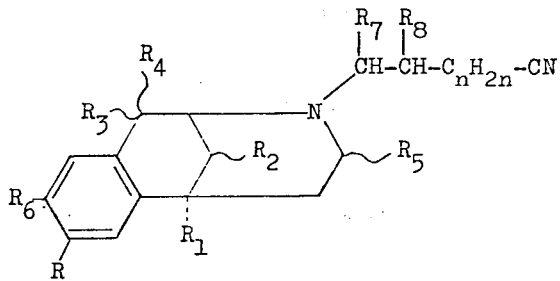

wherein R is a hydrogen atom, a hydroxyl group, a $C^1$ - $C^3$ alkoxy group or a $C^1$ - $C^8$ alkanoyloxy group; $R_1$ is a hydrogen atom, a $C^1$ - $C^5$ alkyl group, a phenyl group, a halophenyl group, an alkylphenyl group wherein the alkyl moiety has 1 to 3 carbon atoms, an alkoxyphenyl group wherein the alkoxy moiety has 1 to 3 carbon atoms, a trifluoromethylphenyl group, an alkylthiophenyl group wherein the alkylthio moiety has 1 to 3 carbon atoms or a group of the formula $(C_mH_{2m-p+1})$ - $(R_9)_p$ wherein $m$ is an integer of 1 - 6, $p$ is an integer of 1 - 2 and $R_9$ is a $C^1$ - $C^3$ alkoxy group; $R_2$ is a hydrogen atom or a $C^1$ - $C^3$ alkyl group; $R_3$ is a hydrogen atom, a $C^1$ - $C^3$ alkyl group, a phenyl group or an alkoxyphenyl group wherein the alkoxy moiety has 1 to 3 carbon atoms; $R_4$ is a hydrogen atom or a hydroxyl group, or $R_3$ and $R_4$ may form a $C^1$ - $C^3$ alkylidene group or a carbonyl group together with a carbon atom to which these substituents are bonded; $R_5$ is a hydrogen atom or a $C^1$ - $C^3$ alkyl group; $R_6$ is a hydrogen atom or a methyl group; $R_7$ and $R_8$ are independently a hydrogen atom or a $C^1$ - $C^2$ alkyl group; and $n$ is an integer of 0 - 2; or an acid addition salt thereof, and a pharmaceutically acceptable carrier or diluent.

2. The composition of claim 1, wherein the benzomorphan derivative has the following formula:

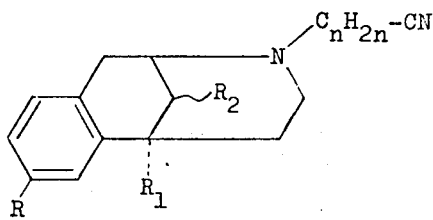

wherein R is a hydrogen atom, a hydroxyl group, a $C^1$ - $C^3$ alkoxy group or a $C^1$ - $C^8$ alkanoyloxy group; $R_1$ is a hydrogen atom, a $C^1$ - $C^5$ alkyl group or a phenyl group; $R_2$ is a hydrogen atom or a $C^1$ - $C^3$ alkyl group; and $n$ is an integer of 2 - 4, or its acid addition salt.

3. The composition of claim 1, wherein the benzomorphan derivative is 2'-hydroxy-2-($\beta$-cyanoethyl)-6,7-benzomorphan.

4. The composition of claim 1, wherein the benzomorphan derivative is 2'-hydroxy-2-($\beta$-cyanoethyl)-5-methyl-6,7-benzomorphan.

5. The composition of claim 1, wherein the benzomorphan derivative is 2'-hydroxy-2-($\beta$-cyanoethyl)-5,9-dimethyl-6,7-benzomorphan.

6. The composition of claim 1, wherein the benzomorphan derivarive is 2'-hydroxy-2-($\beta$-cyanoethyl)-5,9-diethyl-6,7-benzomorphan.

7. The composition of claim 1, wherein the benzomorphan derivative is 2'-acetoxy-2-($\beta$-cyanoethyl)-5,9-dimethyl-6,7-benzomorphan.

8. The composition of claim 1, wherein the benzomorphan derivative is 2'-hydroxy-2-($\gamma$-cyanopropyl)-5,9-dimethyl-6,7-benzomorphan.

9. The composition of claim 1, wherein the benzomorphan derivative is 2'-hydroxy-2-($\gamma$-cyanopropyl)-5-methyl-9-ethyl-6,7-benzomorphan.

10. The composition of claim 1, wherein the benzomorphan derivative is 2'-hydroxy-2-($\gamma$-cyanopropyl)-5-ethyl-9-methyl-6,7-benzomorphan.

11. The composition of claim 1, wherein the benzomorphan derivative is 2'-hydroxy-2-($\gamma$-cyanopropyl)-5,9-diethyl-6,7-benzomorphan.

12. The composition of claim 1, wherein the benzomorphan derivative is 2'-acetoxy-2-($\beta$-cyanoethyl)-5,9-dimethyl-6,7-benzomorphan.

13. The composition of claim 1, wherein the benzomorphan derivative is 2'-acetoxy-2-($\gamma$-cyanopropyl)-5-ethyl-9-methyl-6,7-benzomorphan.

14. The composition of claim 1, wherein the benzomorphan derivative is 2'-methoxy-2-($\gamma$-cyanopropyl)-5-ethyl-9-methyl-6,7-benzomorphan.

15. The composition of claim 1, wherein the benzomorphan derivative is 2'-methoxy-2-($\gamma$-cyanopropyl)-5,9-diethyl-6,7-benzomorphan.

16. The composition of claim 1, wherein the benzomorphan derivative is 2'-hydroxy-2-($\gamma$-cyanopropyl)-5-ethyl-6,7-benzomorphan.

* * * * *